(12) United States Patent
Wang et al.

(10) Patent No.: US 7,531,679 B2
(45) Date of Patent: May 12, 2009

(54) COMPOSITION AND METHOD FOR LOW TEMPERATURE DEPOSITION OF SILICON-CONTAINING FILMS SUCH AS FILMS INCLUDING SILICON NITRIDE, SILICON DIOXIDE AND/OR SILICON-OXYNITRIDE

(75) Inventors: Ziyun Wang, New Milford, CT (US); Chongying Xu, New Milford, CT (US); Ravi K. Laxman, San Jose, CA (US); Thomas H. Baum, New Fairfield, CT (US); Bryan Hendrix, Danbury, CT (US); Jeffrey Roeder, Brookfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 482 days.

(21) Appl. No.: 10/294,431

(22) Filed: Nov. 14, 2002

(65) Prior Publication Data

US 2004/0096582 A1 May 20, 2004

(51) Int. Cl.
*C07F 7/10* (2006.01)
*C23C 14/10* (2006.01)
(52) U.S. Cl. .................. 556/412; 427/255.27
(58) Field of Classification Search .......... 556/410
See application file for complete search history.

(56) References Cited

U.S. PATENT DOCUMENTS

| 5,578,530 | A | 11/1996 | Muroyama et al. |
| 6,013,235 | A * | 1/2000 | Brinson et al. ............ 423/342 |
| 6,383,955 | B1 | 5/2002 | Matsuki et al. |
| 6,410,463 | B1 | 6/2002 | Matsuki |
| 6,936,548 | B2 | 8/2005 | Dussarrat et al. |
| 7,019,159 | B2 | 3/2006 | Dussarrat et al. |
| 7,064,083 | B2 | 6/2006 | Dussarrat et al. |
| 7,132,723 | B2 | 11/2006 | Park et al. |

2004/0138489 A1 7/2004 Wang et al.

FOREIGN PATENT DOCUMENTS

| EP | 1 149 934 B1 | 8/2005 |
| JP | 08-022986 A | 1/1996 |
| WO | 03/046253 | 6/2003 |

OTHER PUBLICATIONS

Yang et al ("Dislane-Catalyzed and Thermally Induced Oligmomerizations of Alkynes: A comparison," Organometallics vol. 19, pp. 893-900, Feb. 2000).*
Söldner et al, "1,2 Disilanediyl Bis(triflate), F3CSO3-SiH2SiH2-O3SCF3, as the Key Intermediate for a Facile Preparation of Open-Chain and Cyclic 1,1- and 1,2-Diaminodisilanes", Inorganic Chemistry vol. 36, pp. 1758-1763, 1997.*
Wan et al (Inorg. Chem. vol. 32, 1993 pp. 341-344; Synthesis of (Dialkylamino)disilanes).*
Heinicke et al; "Aminosubstituted disilanes: synthesis by unsymmetrical and symmetrical reductive coupling"; Heteroatom Chemistry (1998), 9(3), 311-316.*
Heinz Schuh et al. "Disilanyl-amines—Compounds Comprising the Structural Unit Si—Si—N, as Single-Source Precursors for Plasma-Enhanced Chemical Vapour Deposition (PE-CVD) of Silicon Nitride" Z.anorg. allg. Chem. 619 (1993) 1347-1352.
Huppmann, Frank, et al., "English Abstract: Reaktionen subvalenter Verbindungen des Siliciums mit alkylierten Aromaten", "Journal of Oranometallic Chemistry", 1994, pp. 217-228, vol. 483.
Yang, Jinchao, et al., "Synthesis of 1,4-disilacyclohexa-2,5-dienes", "Journal of Organometallic Chemistry", 2002, pp. 276-288, vol. 649.

* cited by examiner

*Primary Examiner*—Elvis O. Price
(74) *Attorney, Agent, or Firm*—Steven J. Hultquist; Intellectual Property/Technology Law; Maggie Chappuis

(57) ABSTRACT

Silicon precursors for forming silicon-containing films in the manufacture of semiconductor devices, such as low dielectric constant (k) thin films, high k gate silicates, low temperature silicon epitaxial films, and films containing silicon nitride ($Si_3N_4$), siliconoxynitride ($SiO_xN_y$) and/or silicon dioxide ($SiO_2$). The precursors of the invention are amenable to use in low temperature (e.g., <500° C.) chemical vapor deposition processes, for fabrication of ULSI devices and device structures.

22 Claims, 7 Drawing Sheets

COMPOSITION AND METHOD FOR LOW TEMPERATURE DEPOSITION OF SILICON-CONTAINING FILMS SUCH AS FILMS INCLUDING SILICON NITRIDE, SILICON DIOXIDE AND/OR SILICON-OXYNITRIDE

FIELD OF THE INVENTION

The present invention relates generally to the formation of silicon-containing films in the manufacture of semiconductor devices, and more specifically to compositions and methods for forming such films, e.g., films comprising silicon, silicon nitride ($Si_3N_4$), siliconoxynitride ($SiO_xN_y$), silicon dioxide ($SiO_2$), etc., low dielectric constant (k) thin silicon-containing films, high k gate silicate films and low temperature silicon epitaxial films.

DESCRIPTION OF THE RELATED ART

In semiconductor manufacturing, thin (e.g., <1,000 nanometers thickness) passive layers of chemically inert dielectric materials, such as silicon nitride ($Si_3N_4$), silicon-oxynitride ($SiO_xN_y$) and/or silicon dioxide ($SiO_2$), are widely employed in microelectronic device structures, to function as structural elements of the multi-layered structure, such as sidewall spacer elements, diffusion masks, oxidation barriers, trench isolation coatings, inter-metallic dielectric materials, passivation layers and etch-stop layers.

Deposition of silicon-containing films by chemical vapor deposition (CVD) techniques is a highly attractive methodology for forming such films. CVD processes involving low deposition temperatures are particularly desired, e.g., temperatures less than about 550° C., but require the availability and use of suitable precursor compositions for such purpose.

Precursors suitable for the formation of dielectric silicon-containing films on semiconductor substrates at low temperatures, e.g., less than about 550° C., must meet the following criteria:

(1) be highly volatile, with liquids having boiling points <250° C. at atmospheric pressure being generally preferred, since higher boiling points make delivery of the precursor disproportionately more difficult for the intended application;

(2) be thermally stable and less hazardous, relative to silanes, disilane and polysilanes, including silicon source compounds such as trichlorosilane and hexachlorodisilane;

(3) have minimum halogen content, to correspondingly minimize formation of particulates and clogging of CVD system pumps by solid byproducts such as quaternary ammonium salts;

(4) preferably be free of direct Si—C bonds, to correspondingly minimize carbon contamination of the product films;

(5) be free of pyrophoricity as well as any susceptibility to detonation and/or rapid decomposition during storage;

(6) preferably have reactive sites consistent with low activation energies in the case of silicon nitride deposition; and (7) have stable organic ligands providing sustained resonance time on the substrate surface to provide high conformality and uniformity of the deposited film, with the organo moiety subsequently being readily liberated, e.g., by a decomposition pathway or co-reaction with another species.

As an example of the foregoing considerations, hexachlorodisilane, $Cl_3Si$—$SiCl_3$, might on initial consideration appear to be a suitable candidate precursor for CVD formation of silicon oxide, silicon oxynitride and/or silicon nitride thin film structures, since it possesses a weak silicon-silicon bond, rendering it ostensibly amenable to use at low CVD process temperatures, but such compound is reported to oxidatively decompose to a shock-sensitive material, and shock, long-term storage and/or high temperature handling may result in spontaneous detonation of the compound. Such adverse potential effects therefore cause hexachlorodisilane to be less preferred for use as a silicon-containing film precursor for forming silicon-containing films, e.g., of silicon oxide, silicon oxynitride and/or silicon nitride, on a substrate.

Among silicon-containing films, silicon nitride poses particular problems. Silicon nitride deposition at temperatures below 500° C. has attracted particular interest for fabrication of microelectronic device structures, such as diffusion barriers, etch-stop layers and side-wall spacers, with tight geometric characteristics and reduced feature size (<130 nanometers). For the next generation of ultra-large scale integration (ULSI) devices, deposition precursors and processes are desired that accommodate deposition of silicon nitride films at temperatures not exceeding about 450° C. Currently used precursors, e.g., BTBAS or silane/ammonia, typically require temperatures above 600° C. to form high quality $Si_3N_4$ films.

The art therefore has a continuing need for improved precursors amenable to deposition methods such as chemical vapor deposition, for forming silicon-containing films of the aforementioned types.

SUMMARY OF THE INVENTION

The present invention relates generally to the formation of silicon-containing films in the manufacture of semiconductor devices, and more specifically to compositions and methods for forming such silicon-containing films, such as films comprising silicon, silicon nitride ($Si_3N_4$), siliconoxynitride ($SiO_xN_y$), silicon dioxide ($SiO_2$), etc., silicon-containing low k films, high k gate silicates, and silicon epitaxial films.

The present invention in one aspect relates to a silicon compound selected from the group consisting of:

(A) compounds of the formula:

$$[SiX_n(NR^1R^2)_{3-n}]_2 \qquad (1)$$

wherein:

$R^1$ and $R^2$ may be the same as or different from one another and each is independently selected from the group consisting of H, $C_1$-$C_5$ alkyl, and $C_3$-$C_6$ cycloalkyl;

X is selected from the group consisting of halogen (e.g., bromine, fluorine and chlorine), hydrogen and deuterium; and $0 \leq n \leq 2$;

(B) compounds of the formula

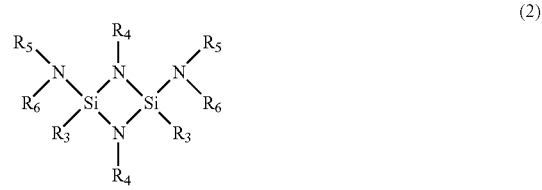

(2)

wherein:

each of $R_3$ can be the same as or different from the other and each is independently selected from the group consisting of H, $C_1$-$C_4$ alkyl, and $C_3$-$C_6$ cycloalkyl; and each of $R_4$, $R_5$ and $R_6$ can be the same as or different from the others and each is independently selected from the group consisting of H, $C_1$-$C_4$ alkyl, $C_3$-$C_6$ cycloalkyl, $Si(CH_3)_3$ and $SiCl_3$;

(C) metal source reagent complexes formed by metal cation reaction with deprotonated anionic forms of the compounds (B);

(D) disilicon cycloamides of the formulae (3)-(6):

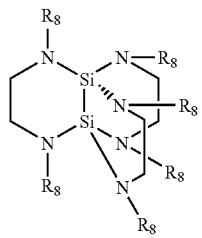

(3)

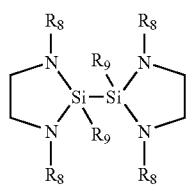

(4)

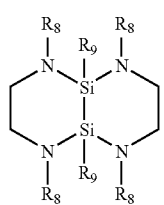

(5)

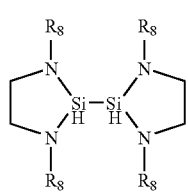

(6)

wherein:

each of $R_8$ can be the same as or different from the others and each is independently selected from the group consisting of H, $C_1$-$C_4$ alkyl, and $C_3$-$C_6$ cycloalkyl; and each of $R_9$ can be the same as or different from the others and each is independently selected from the group consisting of H and $NR_8H$ where $R_8$ is as defined above; and (E) cyclosilicon compounds of the formula:

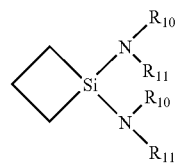

(7)

wherein:

each of $R_{10}$ and $R_{11}$ can be the same as or different from the others and each is independently selected from the group consisting of H, $C_1$-$C_4$ alkyl, and $C_3$-$C_6$ cycloalkyl.

In another aspect, the invention relates to a method of forming a silicon-containing film on a substrate, comprising contacting a substrate under chemical vapor deposition conditions including temperature below 600° C. with a vapor of a silicon compound of a type as described above.

Another aspect of the invention relates to a method of making a silicon compound of the formula $$[SiX_n(NR^1R^2)_{3-n}]_2 \quad (1)$$

wherein:

$R^1$ and $R^2$ may be the same as or different from one another and each is independently selected from the group consisting of H, $C_1$-$C_5$ alkyl, and $C_3$-$C_6$ cycloalkyl;

X is selected from the group consisting of halogen (e.g., bromine, fluorine and chlorine), hydrogen and deuterium; and $0 \leq n \leq 2$, such method comprising reacting a disilane compound of the formula $X_3Si$—$SiX_3$ with an amine ($R^1R^2NH$) or lithium amide (($R^1R^2N$)Li compound, wherein X, $R^1$ and $R^1$ are as set out above, according to a reaction selected from the group consisting of the following reactions:

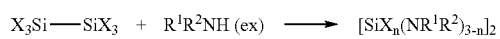

(A)

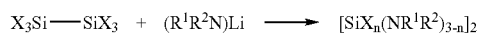

(B)

A still further aspect of the invention relates to a method of forming a metal, metal nitride or metal oxide film on a substrate, comprising contacting said substrate with a precursor metal complex formed by ionic reaction of metal cation with a deprotonated anionic form of a silicon compound of the formula (2) above, e.g., a compound such as

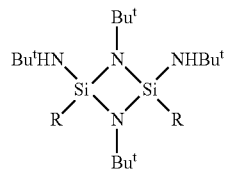

(2)

wherein each of the R substituents may be the same as or different from the other and each is independently selected from the group consisting of H, $C_1$-$C_4$ alkyl, and $C_3$-$C_6$ cycloalkyl.

Yet another aspect of the invention relates to a method of forming a silicon nitride film on a substrate by chemical vapor deposition, comprising contacting said substrate with vapor of silicon source and nitrogen source compounds, wherein said nitrogen source compounds are other than nitrogen or ammonia, and said chemical vapor deposition is conducted at temperature <550° C., wherein said nitrogen source compound is selected from the group consisting of R-diazo compounds, wherein R is H, $C_1$-$C_4$ alkyl or $C_3$-$C_6$ cycloalkyl, triazoles, tetrazoles, amadines, silylazides, small ring nitrogen compounds, and molecules including organic acyclic or cyclic moieties that contain one or more —N—N bonds.

Still another aspect of this invention relates to a method of forming a silicon epitaxial layer on a substrate at low temperature, e.g., a temperature below about 600° C., and preferably below 550° C., by contacting the substrate with a silicon precursor in the presence of a substantial excess of a reducing agent, such as hydrogen, silane ($SiH_4$) or disilane ($Si_2H_6$).

Other aspects, features and embodiments of the invention will be more fully apparent from the ensuing disclosure and appended claims.

Figure 1:
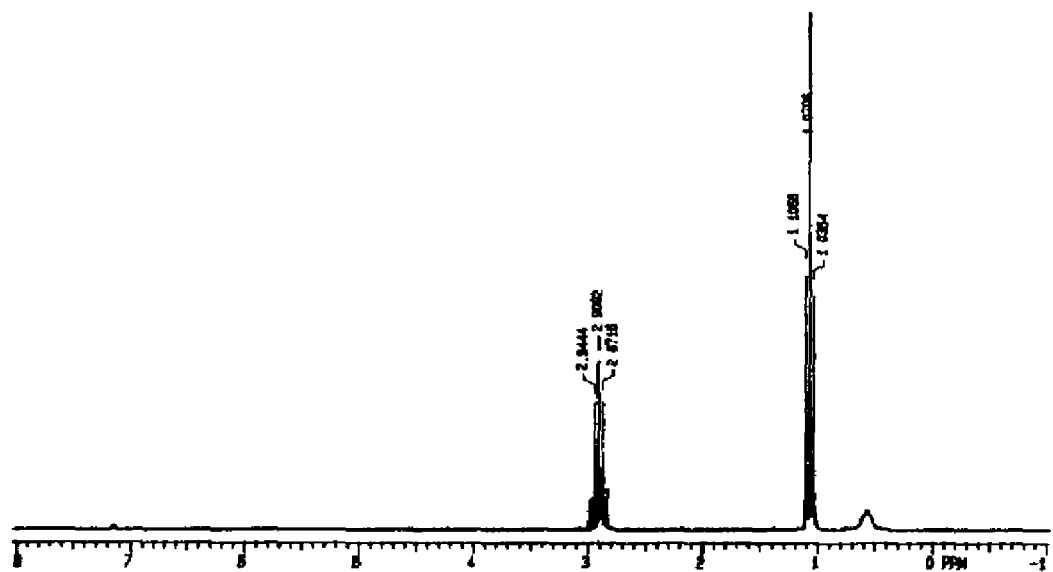
FIG. 1 is an $^1H$ NMR spectrum of $(HNEt)_3Si$—$Si(HNEt)_3$.

DETAILED DESCRIPTION OF THE INVENTION
AND PREFERRED EMBODIMENTS THEREOF

The present invention relates to silicon precursors for CVD formation of films on substrates, such as silicon precursors for forming low k dielectric films, high k gate silicates, low temperature silicon epitaxial films, and films comprising silicon, silicon oxide, silicon oxynitride, silicon nitride, etc., as well as to corresponding processes for forming such films with such precursors.

In one aspect, the invention provides as such precursor a compound of the formula:

$$[SiX_n(NR^1R^2)_{3-n}]_2 \tag{1}$$

wherein:
$R^1$ and $R^2$ may be the same as or different from one another and each is independently selected from the group consisting of H, $C_1$-$C_5$ alkyl, and $C_3$-$C_6$ cycloalkyl;
X is selected from the group consisting of halogen (e.g., bromine, fluorine and chlorine), hydrogen and deuterium; and
$0 \leq n \leq 2$.

One preferred class of compounds of formula (1) has the formula:

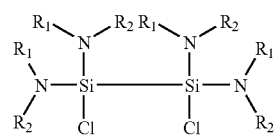

wherein R1 and R2 are as defined in connection with formula (1).

The compounds of formula (1) are usefully employed for forming films on substrates, e.g., by chemical vapor deposition at temperature <500° C. The films that can be formed using such precursor compounds include low dielectric constant (k) thin films, high k gate silicates and silicon epitaxial films. In one aspect of the invention, the films formed using such precursors comprise silicon, silicon oxide, silicon oxynitride and/or silicon nitride.

Preferred compounds of formula (1) include $(Et_2N)_2ClSi$—$SiCl(NEt_2)_2$, $(EtNH)_3Si$—$Si(HNEt)_3$, $(Bu^tNH)_2ClSi$—$SiCl(HNBu^t)_2$, $(Me_2N)_2ClSi$—$SiCl(NMe_2)_2$, $Cl_2HSi$—$SiHCl_2$, $(EtNH)_2HSi$—$SiH(NHEt)_2$, and the like.

Compounds of formula (1) are readily synthesized by reaction of disilane compounds of the formula $X_3Si$—$SiX_3$ with amine ($R^1R^2NH$) or lithium amide (($R^1R^2N$)Li) compounds, wherein X, $R^1$ and $R^2$ are as set out above, according to following reactions:

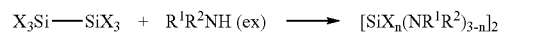

$$X_3Si\text{---}SiX_3 + R^1R^2NH \text{ (ex)} \longrightarrow [SiX_n(NR^1R^2)_{3-n}]_2 \tag{A}$$

$$X_3Si\text{---}SiX_3 + (R^1R^2N)Li \longrightarrow [SiX_n(NR^1R^2)_{3-n}]_2 \tag{B}$$

as hereinafter more fully described in the examples herein.

In specific applications, it may be necessary or desirable to conduct a second reaction to introduce hydrogen in place of the halogen.

The invention in another aspect provides a further class of silicon precursor compounds, comprising nitrogen-containing cyclosilicon compounds of the formula:

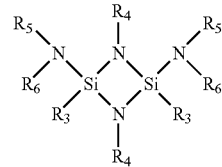

(2)

wherein:
each of $R_3$ can be the same as or different from the other and each is independently selected from the group consisting of H, $C_1$-$C_4$ alkyl, and $C_3$-$C_6$ cycloalkyl; and
each of $R_4$, $R_5$ and $R_6$ can be the same as or different from the others and each is independently selected from the group consisting of H, $C_1$-$C_4$ alkyl, $C_3$-$C_6$ cycloalkyl, $Si(CH_3)_3$ and $SiCl_3$.

A preferred class of compounds of formula (2) includes the compounds of formula (2a):

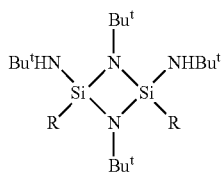
(2a)

wherein each of the R substituents may be the same as or different from the other and each is independently selected from the group consisting of H, $C_1$-$C_4$ alkyl, and $C_3$-$C_6$ cycloalkyl. In one preferred compound of such type, both R substituents are hydrogen. In another preferred compound of such type, both R substituents are methyl.

The precursors of formula (2a) contain two silicon atoms in a four-member ring structure with four tertiary butyl ($Bu^t$) groups on the nitrogen atoms. In such compositions, as employed for chemical vapor deposition of silicon nitride, the tertiary butyl groups are effective leaving groups, so that there is minimal $Bu^t$-associated carbon incorporation into films formed from such precursors. In one preferred aspect of the invention, such precursors are usefully employed in low temperature (<500° C.) CVD processes as precursors for silicon nitride films.

With reference to the silicon compounds of formula (2a), another class of compounds of the present invention includes those corresponding to formula (2a) but wherein the tertiary butyl ($Bu^t$) groups are replaced by trimethylsilyl (—$SiMe_3$) or trichlorosilyl (—$SiCl_3$) groups.

The precursors of formulae (2) and (2a) can be advantageously employed as ligands to form corresponding metal complexes, by deprotonation reaction serving to remove the hydrogen substituents of hydrogen-bearing groups, e.g., the tertiary butyl ($Bu^t$) groups on the nitrogen atoms in formula (2a), to form corresponding anionic species, followed by reaction of the anionic species with metal cations (which can be any metal or transition metal of the Periodic Table, e.g., hafnium (Hf), zirconium (Zr), barium (Ba), etc.) to form corresponding neutral metal source reagent complexes. Such metal source reagent complexes are usefully employed as CVD precursors for metal nitrides, metal oxides and pure metal films.

The precursors of formula (2) and their corresponding metal complexes are usefully employed for forming thin films on substrates by chemical vapor deposition.

Another class of silicon precursors in accordance with the invention, which are amenable to CVD use at low temperatures, such as in the range of from about 350° C. to about 550° C. for pre and post metal deposition of thin (e.g., 500 Angstroms to 1 micrometer thickness) dielectric films of silicon nitride or silicon dioxide in semiconductor manufacturing, or otherwise for forming silicon nitride or silicon dioxide ceramic thin films as well as films on different substrates, at temperatures in the range of from about 100° C. to about 600° C., comprise the disilicon cycloamides of the formulae (3)-(6):

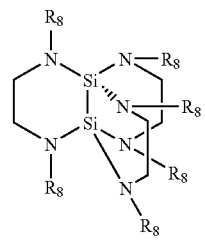
(3)

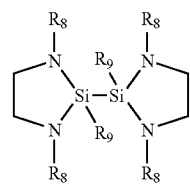
(4)

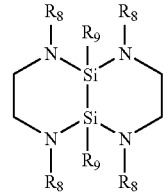
(5)

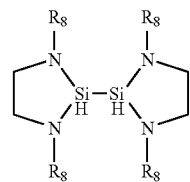
(6)

wherein:
each of $R_8$ can be the same as or different from the others and each is independently selected from the group consisting of H, $C_1$-$C_4$ alkyl, and $C_3$-$C_6$ cycloalkyl; and
each of $R_9$ can be the same as or different from the others and each is independently selected from the group consisting of H and $NR_8H$ where $R_8$ is as defined above.

Another class of compounds useful as silicon precursors in the practice of the invention include those of formula (7):

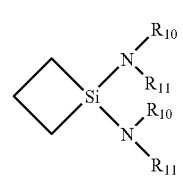
(7)

wherein:
each of $R_{10}$ and $R_{11}$ can be the same as or different from the others and each is independently selected from the group consisting of H, $C_1$-$C_4$ alkyl, and $C_3$-$C_6$ cycloalkyl.

One preferred compound of those of formula (7) is the cyclosilicon compound wherein each of $R_{10}$ and $R_{11}$ is tertiary butyl ($Bu^t$).

The compounds of formulae (1)-(7) can be reacted with suitable co-reactants at relatively low activation energies, as for example in accordance with the reaction scheme (C) shown below:

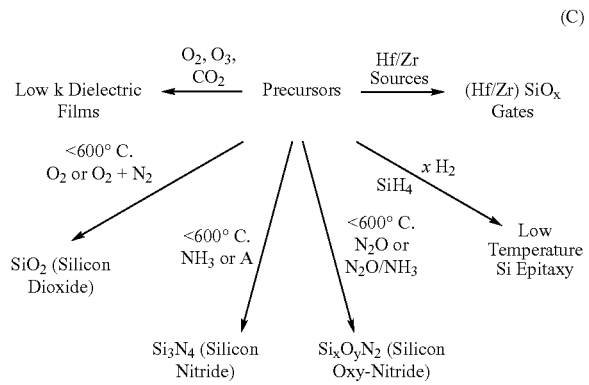

(C)

In reaction scheme (C), "Precursors" are any of the precursor compounds of formulae (1)-(7). The co-reactant can be (i) oxygen, ozone or $CO_2$ to form low k dielectric films, (ii) oxygen or a combination of oxygen and nitrogen at deposition temperature <600° C. to form silicon dioxide, (iii) ammonia "or A," wherein "A" is selected from the group consisting of $R_3Si-N_3$, $R-N=NR'$ and $R-N=N^+=NR'$, each R is independently selected from the group consisting of $C_1-C_3$ alkyl substituents, R' is R or H, and such co-reactant species is employed at deposition temperature <600° C. to form silicon nitride, (iv) dinitrogen oxide (nitrous oxide, $N_2O$), or a mixture of nitrous oxide and ammonia, at temperature <600° C., to form silicon oxynitride, (v) hydrogen and silane, for low temperature silicon epitaxy, and (vi) hafnium and/or zirconium sources, in the presence of oxygen and nitrous oxide, to form silicate gate structures.

In accordance with reaction scheme (C), the type of dielectric film produced by the corresponding CVD process can be tailored by choice of the specific co-reactant. For example, hydrogen, ammonia, oxygen or nitrous oxide may be used as alternative single reactants to form the respective silicon nitride, silicon dioxide or silicon oxynitride single component films, or a mixture of two or more of such reactants can be employed in the CVD process with selected one(s) of the formulae (1)-(7) precursors to form corresponding multicomponent films, or graded composition films. Other co-reactants may be added to introduce other elemental species (e.g., hafnium, zirconium, barium, titanium, tantalum, etc.).

In a further aspect, the invention relates to a method of forming a silicon epitaxial layer on a substrate at temperature below about 600° C., preferably less than about 550° C., by contacting the substrate with a silicon precursor in the presence of a substantial excess of a reducing agent, e.g., a reducing agent such as hydrogen, silane ($SiH_4$), disilane ($Si_2H_6$), etc.

A further aspect of the invention relates to the use of silicon source compounds with nitrogen source compounds other than nitrogen or ammonia that afford lower activation energy formation of silicon nitride on a substrate, at temperatures <550° C. The use of such alternative co-reactant nitrogen source compounds overcomes the difficulty of depositing silicon nitride at reasonable deposition rates at temperature below 550° C. due to the high activation energy required for nitrogen or ammonia to form Si—N bonds in such low temperature regime.

The use of low activation energy co-reactant nitrogen source compounds permits silicon source compounds that would otherwise be unacceptable in use with ammonia or nitrogen, to be efficiently employed to deposit silicon-containing and nitrogen-containing films at temperatures <550° C. Low activation energy co-reactant nitrogen source compounds for such purpose can be of any suitable type, including for example R-diazo compounds, wherein R is H, $C_1-C_4$ alkyl or $C_3-C_6$ cycloalkyl, triazoles and tetrazoles, amadines, silylazides, small ring nitrogen compounds such as aziridines, or molecules including organic acyclic or cyclic moieties that contain one or more —N—N bonds.

In use, co-reactants of the foregoing types are introduced to the CVD reactor as reactive gases, along with the silicon source compound(s). Co-reactant reactive gases of such types, comprising compounds that contain multiple nitrogen atoms, can be used with reactive disilanes such as hexachlorodisilane that would otherwise be wholly unsuitable for formation of silicon nitride films at temperatures <550° C. In such usage, particulate formation is controlled under optimized CVD process conditions to eliminate particle-generating homogenous gas-phase reactions.

In application of the co-reactant reaction scheme (C), the silicon-containing precursor is reacted with a desired co-reactant in any suitable manner, e.g., in a single wafer CVD chamber, or in a furnace containing multiple wafers, utilizing process conditions including temperature <550° C. and appertaining pressures, concentrations, flow rates and CVD techniques, as readily determinable within the skill of the art for a given application, based on the disclosure herein.

By way of example, in the application of such co-reactant scheme, silicon nitride films can be deposited by deposition techniques such as atomic layer deposition (ALD) involving sequenced pulses wherein the two or more reactants are sequentially introduced to react on the surface bearing the adsorbed reactant species, to form one monolayer of the SiN film at a time.

Alternatively, silicon nitride films can be formed by low-pressure CVD techniques, e.g., by a single-wafer deposition process at pressure in a range of from about 1 to about 1000 torr, or in a batch deposition furnace procedure at low pressure such as pressure ≦4 torr, involving chemical reactions that take place in a pressure range of from about 100 mtorr to 4 torr.

An illustrative low-pressure chemical vapor deposition (LPCVD) process is described below.

In the first step of such illustrative LPCVD process, reactants are introduced into the reaction chamber. Such reactants can be diluted with inert gases, if and as needed, to facilitate reaction control and homogeneous mixing. The reactants are diffused onto the substrate and are adsorbed on the substrate surface.

In a second step of the LPCVD process, the reactants adsorbed on the substrate undergo migration and/or chemically react on the surface, with gaseous byproducts of the reaction being desorbed to leave behind the deposited film.

The co-reactant deposition may be carried out to form silicon nitride, silicon dioxide or silicon oxynitride films in any suitable reactor, e.g., a vertical flow isothermal LPCVD reactor. A vertical reactor is usefully employed to avoid wafer-to-wafer reactant depletion effects; such reactor does not require temperature ramping, and produces highly uniform deposited films.

The vacuum system utilized for providing the low pressure condition of the LPCVD process can be of any suitable type, and can for example include a dry pump or rotary vane pump/roots blower combination and various cold traps if and as needed. Reactor pressure can be controlled by a capacitance manometer feedback to a throttle valve controller.

Use of a conventional LPCVD system to carry out reactions of the co-reactant scheme (C), at reactor loadings of eighty 200 or 300 mm diameter silicon wafers at 4-9 mm spacing, produced a uniform conductance around the wafer peripheries by compensating for conductance restrictions attributable to the boats and the sled in such system. The temperature uniformity across the wafer load was ±1° C. as measured by an internal multi-junction thermocouple. Deposition uniformity down the wafer load was improved by employing a temperature ramp. Changing the reactant to precursor ratios from 100:1 to 1:1 optimized deposition conditions. The pressure was typically below 1 torr, being varied from 100 mtorr to 1 torr, and the optimum deposition temperature was in a range of from about 100° C. to about 550° C. In general, the invention may be carried out with delivery of precursors in neat form, via liquid delivery, or bubbler or vaporizer. Solvents can be employed for liquid delivery, such as organic solvents, e.g., amine solvents such as $NR_xH_{3-x}$, wherein R is H or $C_1$-$C_4$ alkyl, etc.

As another example of specific precursors useful in the general practice of the invention to form silicon-containing films, such as silicon, silicon oxide, silicon nitride, and silicon oxynitride films, silicate gate materials and low k dielectrics, tetrakisdiethylamidodichlorodisilane, $(NEt_2)_2ClSi$—$SiCl(NEt_2)_2$ is a precursor containing a silicon-silicon bond with only two chlorines in the molecule, and amido groups which are efficient leaving groups in the formation of silicon-containing films having a low carbon contamination characteristic.

Tetrakisdiethylamidodichlorodisilane is readily synthesized as hereinafter more fully described in Example 5 hereof, and is usefully employed to form silicon-containing films of good quality, such as films of silicon, silicon oxide, silicon nitride, silicon oxynitride, etc., by low pressure CVD.

The features and advantages of the invention are more fully shown by the following illustrative and non-limiting examples.

EXAMPLE 1

Synthesis of $(HNEt)_3Si$—$Si(HNEt)_3$

Figure 2:
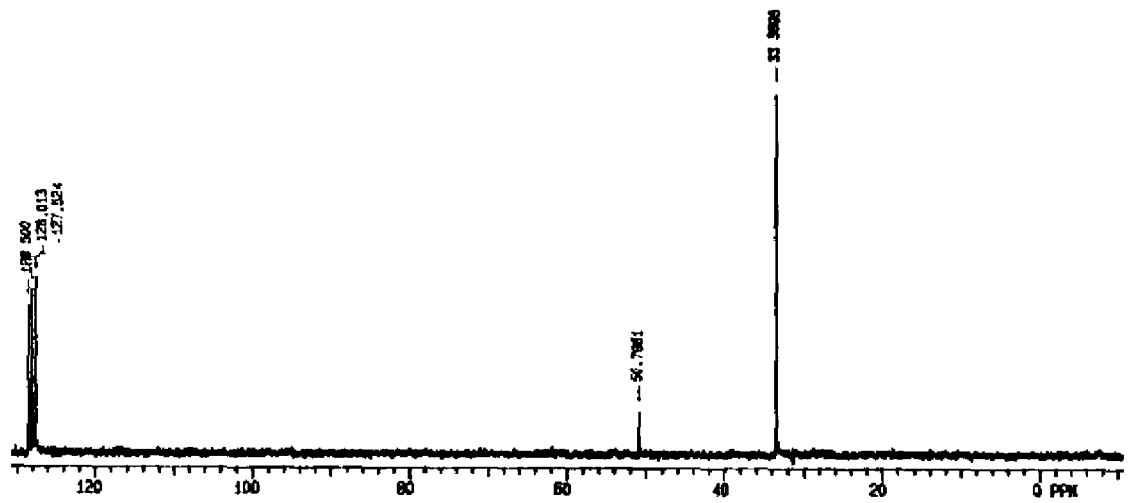
FIG. 2 is a $^{13}C$ NMR spectrum of $(HNEt)_3Si$—$Si(HNEt)_3$.
Figure 3:
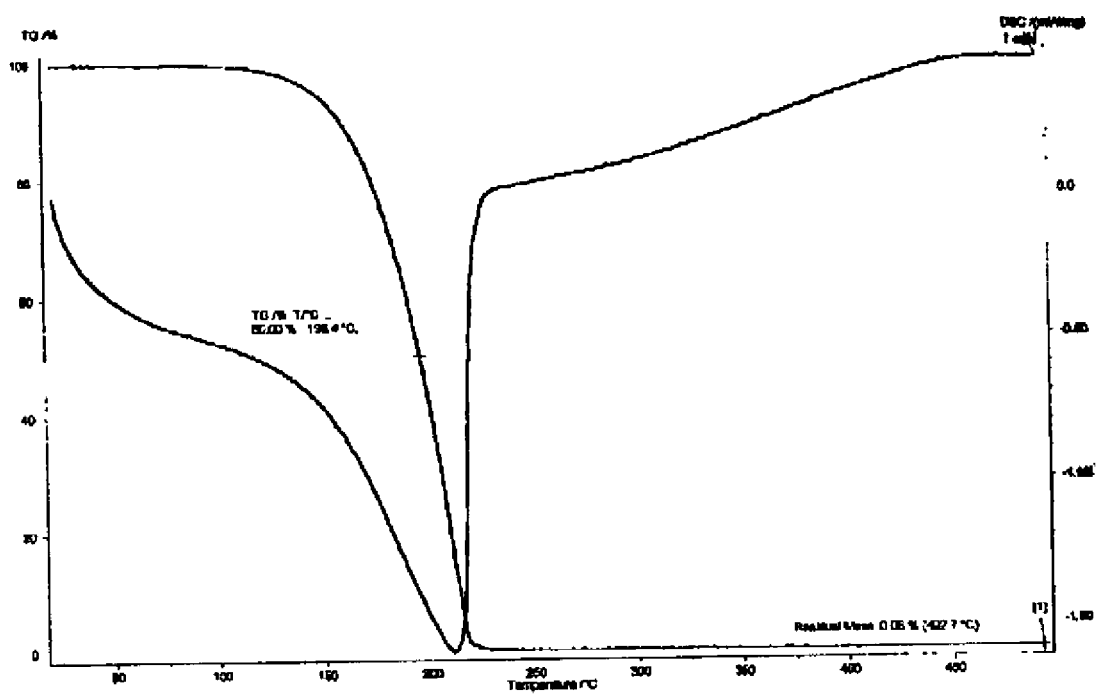
FIG. 3 is an STA plot for $(HNEt)_3Si$—$Si(HNEt)_3$.

In a 5 L flask, 152 g (0.565 mol) of $Cl_3SiSiCl_3$ was added with 4 L of hexanes. The flask was cooled to 0° C. using an ice-bath. $EtNH_2$ (400 g, 8.87 mol; b.p.32° C.) was added to the flask under magnetic stirring. White precipitate material was observed immediately. Upon completion of the addition, the ice-bath was removed and the flask was allowed to warm up to room temperature. The reaction mixture was kept stirring overnight and then refluxed for another two hours. After the reaction mixture was cooled to room temperature, it was filtered through a glass frit filter. The solvent was removed from the filtrate under vacuum. Crude product (152 g) was obtained (84% yield). The pure product $((HNEt)_3Si$—$Si(HNEt)_3)$ was obtained from fractional distillation at about 95° C. under 120 mtorr. Shown in FIGS. 1 and 2 are the $^1H$—and $^{13}C$-NMR spectra respectively. FIG. 3 shows the STA data. $^1H$ NMR ($C_6D_6$): δ 0.67 (br, 6H, N-H), 1.07 (t, 18H), 2.91 (p, 12H); $^{13}C$ {$^1H$} NMR ($C_6D_6$): δ 20.8 ($CH_3$), 35.9 ($CH_2$); $C_{12}H_{36}N_6Si_2$ Calcd: C, 44.95; H, 11.32; N, 26.21; Found: C, 44.69; H, 10.75; N, 25.85.

The STA data showed the $T_{50}$ value of $(HNEt)_3Si$—$Si(HNEt)_3$ to be about 185° C., evidencing good volatility and transport properties for chemical vapor deposition.

EXAMPLE 2

Synthesis of $(Bu^tNH)_2ClSi$—$SiCl(HNBu^t)_2$

Figure 4:
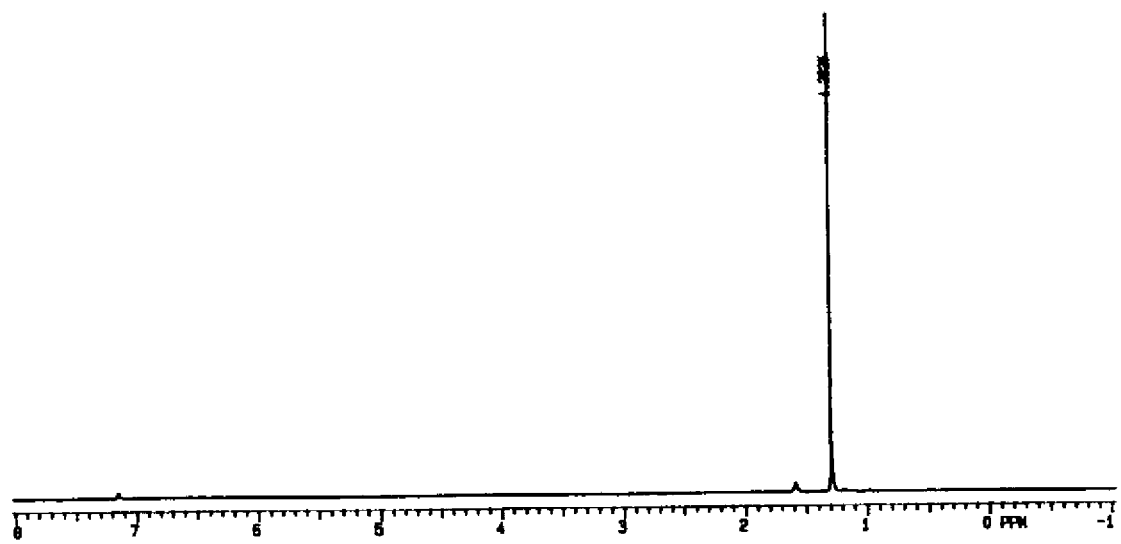
FIG. 4 is an $^1H$ NMR spectrum of $(Bu^tNH)_2ClSi$—$SiCl(HNBu^t)_2$.
Figure 5:
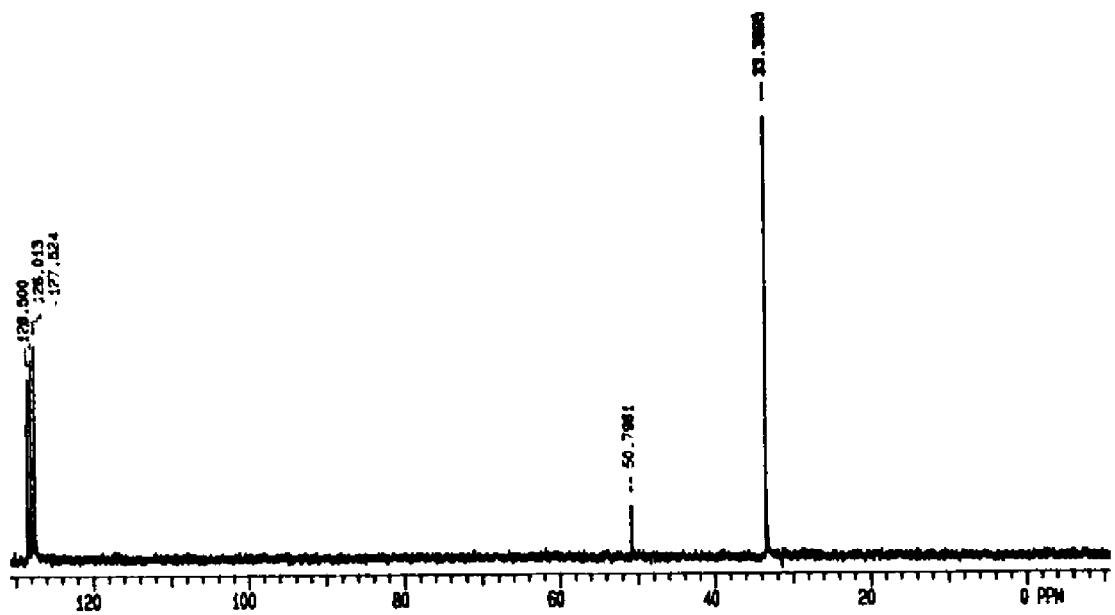
FIG. 5 is a $^{13}C$ NMR spectrum of $(Bu^tNH)_2ClSi$—$SiCl(HNBu^t)_2$.
Figure 6:
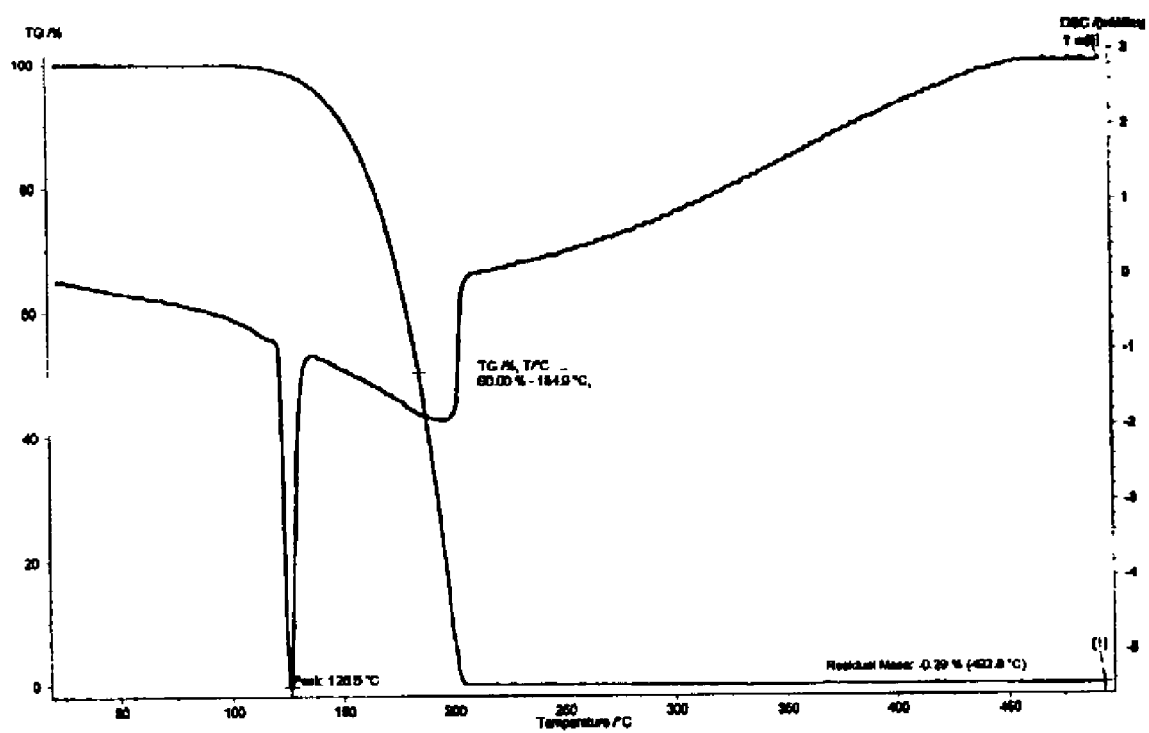
FIG. 6 is an STA plot for $(Bu^tNH)_2ClSi$—$SiCl(HNBu^t)_2$.

In a 250 mL flask with 180 mL of diethyl ether, 5 g (18.6 mmol) of $Cl_3SiSiCl_3$ was added. The flask was cooled to 0° C. in an ice-bath. Under magnetically stirring, $Bu^tNH_2$ (13.6 g/186 mmol) in 30 mL of ether was added into the flask dropwise. White precipitate material was formed immediately. Upon completion of the addition, the ice-bath was removed and the flask was allowed to warm up to room temperature. The reaction mixture was stirred overnight and then refluxed for another two hours. After the reaction mixture was cooled to room temperature, it was filtered through a frit filter. Removal of volatiles from the filtrate gave 6.10 g of white solid crude product in 79% yield. It can further purified by recrystallization from its hexanes-THF mixture solution at 0° C. The crystals have been characterized by X-ray analysis. Shown in FIGS. 4 and 5 are the $^1H$—and $^{13}C$—NMR spectra, respectively. FIG. 6 shows the STA data for the product, $(Bu^tNH)_2ClSi$—$SiCl(HNBu^t)_2$, which had a $T_{50}$ value of about 196° C., evidencing good volatility and transport properties for chemical vapor deposition.

$^1H$ NMR ($C_6D_6$): δ 1.28 (s, 36H), 1.59 (br, 4H, N—H), $^{13}C$ {$^1H$} NMR ($C_6D_6$): δ 33.4 ($CH_3$), 50.8 (C); $C_{16}H_{40}Cl_2N_4Si_2$ Calcd: C, 46.24; H, 9.70; N, 13.48; Found: C, 45.98; H, 9.99; N, 13.14.

EXAMPLE 3

Synthesis of $(Bu^tNH)_2Si(H)Cl$

Figure 7:
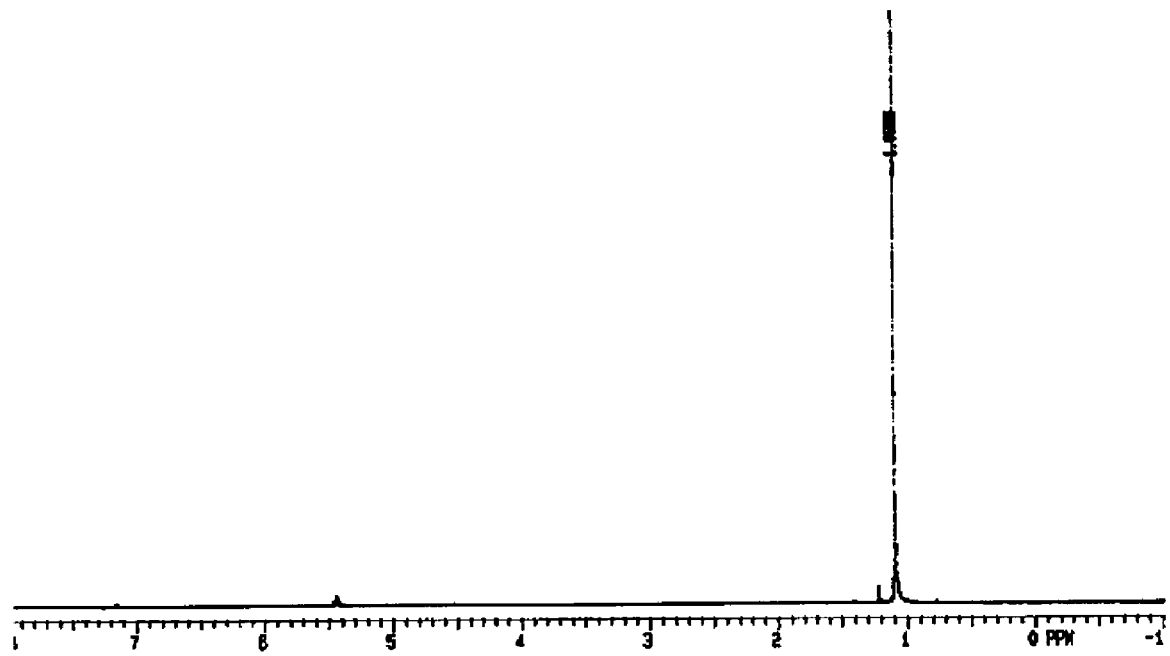
FIG. 7 is an $^1H$-NMR spectrum of $(Bu^tNH)_2Si(H)Cl$ in $C_6D_6$.

The general reactions were carried out under a steady flow of nitrogen. A 500 mL Schlenk flask equipped a magnetic stirring bar, was charged with 250 mL of dry ether and 21.6 g of $^tBuNH_2$ and. To this flask, 10 g, 73.8 mmol of $HSiCl_3$ in 50 mL of ether was added dropwise at 0° C. Upon completion of the addition, the mixture was stirred overnight. The mixture was then refluxed for an additional 4 hours. It was cooled to room temperature and filtered through Celite®. Solvents were removal of by quick distillation or vacuum. The crude yield was 80%. It was then purified by fractional vacuum distillation to around 98% in purity. The product, $(Bu^tNH)_2Si(H)Cl$, was characterized by solution NMR in $C_6D_6$ (FIG. 7). $^1H$ NMR ($C_6D_6$), δ (ppm), 5.48 (t, 1H), 1.09 (s, 18H).

EXAMPLE 4

Synthesis of η-(N,N-t-butyl)-di(t-butylamino)cyclodisilane

Figure 8:
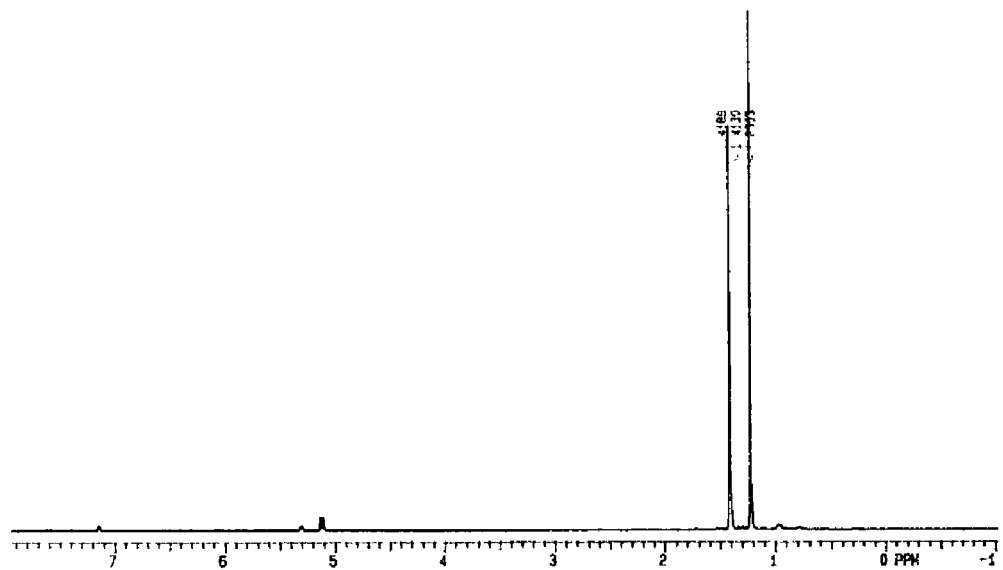
FIG. 8 is an $^1H$-NMR spectrum of η-(N,N-t-butyl)-di(t-butylamino)cyclodisilane in $C_6D_6$.
Figure 9:
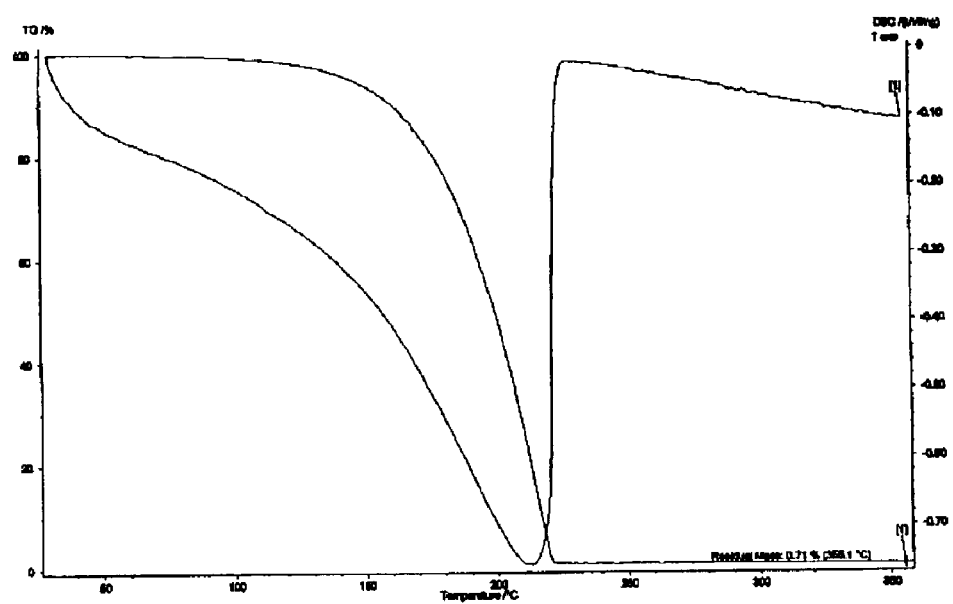
FIG. 9 is an STA plot for η-(N,N-t-butyl)-di(t-butylamino) cyclodisilane.

The general reactions were carried out under a steady flow of nitrogen using Schlenk techniques. A 250 mL Schlenk flask was charged with 9.22 g, 44.2 mmol of di(tert-butylamino)(chloro)silane in 150 mL of hexanes and a stir bar. Then 26 mL of 1.7 M tert-butyllithium solution in patane was added into the Schlenk flask slowly at 0° C., under magnetic stirring. A white precipitate of LiCl formed during the addition. Upon completion of the addition, the mixture was refluxed overnight. The reaction mixture was then allowed to cool and filtered through Celite® to obtain a slightly yellow clear solution. All volatiles were removed under vacuum and the crude yield was about 60%. This crude product was purified by vacuum column distillation. The pure product was received while the oil bath temperature was set to 170° C. and the vacuum at 200 mtorr. It was characterized by solution NMR in $C_6D_6$ (FIG. 8) and STA (FIG. 9). $^1$H-NMR ($C_6D_6$), δ (ppm), 5.31 (dd, 2H, cis or trans isomer), 5.12 (d, 2H, cis or trans isomers), 1.42 (s, 18H, cis or trans isomer), 1.41 (s, 18H, cis or trans isomer) and 1.24 (s, 18H, both isomers).

EXAMPLE 5

Synthesis of $(NEt_2)_2ClSiSiCl(NEt_2)_2$

In a 250 mL flask with 180 mL of ether, 5 g, 18.6 mmol of $Cl_3SiSiCl_3$ was added. The flask was cooled to 0° C. using an ice-bath. While kept stirring, $Et_2NH_2$, 16.3 g, 223 mmol in 30 mL of ether was added dropwise into the flask. Upon completion of addition, the ice-bath was removed and the flask was allowed to warm up to room temperature. The reaction mixture was kept stirring overnight and then refluxed for another two hours. After the reaction mixture was cooled to room temperature, it was filtered through a frit filter. The solvent was removed from the filtrate by vacuum. The product tetrakisdiethylamidodichlorodisilane was obtained from column distillation while controlling the oil bath temperature at around 165° C. 6.35 g, 15.2 mmol product, $(NEt_2)_2ClSiSiCl(NEt_2)_2$, was obtained which corresponded to 82% yield. $^1$H NMR in $C_6D_6$: 1.05 (t, 16H), 3.02 (q, 24H). $C_{16}H_{40}Cl_2N_4Si_2$ Calcd: C, 46.24; H, 9.70; N, 13.48; Found: C, 46.17; H, 9.73; N, 13.33.

EXAMPLE 6

Silicon Nitride Deposition From $(HNEt)_3Si—Si(HNEt)_3$

Figure 10:
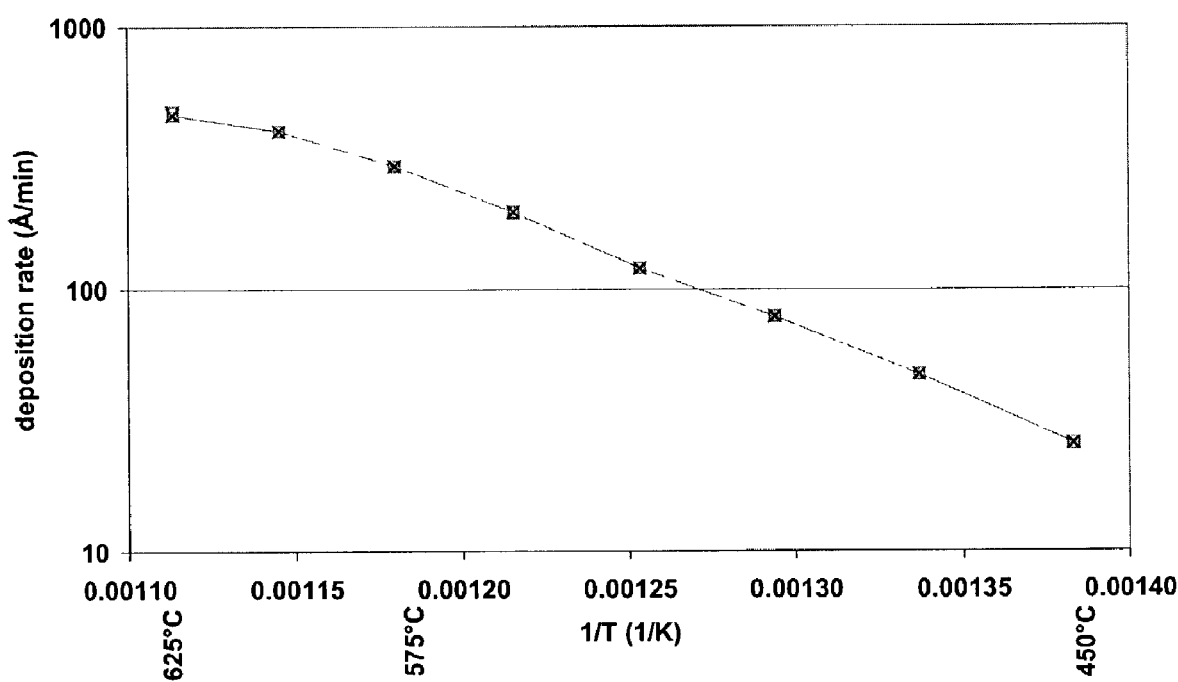
FIG. 10 is a plot of deposition rate as a function of temperature for $(HNEt)_3Si$—$Si(HNEt)_3$ at 10 torr, 10 sccm $NH_3$, 10 sccm He, and 0.1 ml/minute.

A solution of the compound of Example 1, $(HNEt)_3Si—Si(HNEt)_3$, was prepared at a concentration of 0.4M in a hydrocarbon solvent. This solution was metered at 0.1 ml/minute into a vaporizer that was held at temperature of 120° C. and had a flow of 10 standard cubic centimeters per minute (sccm) of He as a carrier gas. The vapor was mixed with 10 sccm of $NH_3$ in a showerhead vaporizer device that was maintained at 120° C. and thereby dispersed over the surface of a heated Si(100) wafer. The chamber pressure was maintained at 10 torr during deposition. The growth rate of the silicon nitride films decreased from 470 Å/minute at a wafer temperature of 625° C. to 26 Å/minute at 450° C. as shown in FIG. 10.

Chemical analysis of the films, by a combination of RBS (Rutherford Backscattering), HFS (Hydrogen Forward Scattering), and NRA (Nuclear Reaction Analysis), revealed that higher pressures and higher $NH_3$ flows increased the N/Si ratio to the stoichiometric value of 1.33 and decreased the impurity carbon content as shown in Table 1 below.

TABLE 1

Film composition for various deposition conditions using the precursor $(HNEt)_3Si—Si(HNEt)_3$.

| NH3 (sccm) | T (° C.) | P (torr) | Rate (Å/min) | n | H (at %) | C (at %) | O (at %) | N/Si |
|---|---|---|---|---|---|---|---|---|
| 10 | 550 | 10 | 196 | 1.87 | 20.5 | 13.5 | 13.3 | 1.15 |
| 100 | 530 | 40 | 72 | 1.78 | 25.5 | 5.2 | 11.2 | 1.31 |
| 100 | 530 | 80 | 59 | 1.79 | 21.5 | 5 | 5.9 | 1.37 |
| 140 | 624 | 80 | 184 | 1.84 | 14.5 | 3.6 | 0.9 | 1.36 |

EXAMPLE 7

Silicon Nitride Deposition with a Pulsed Process From $(HNEt)_3Si—Si(HNEt)_3$ $(HNEt)_3Si—Si(HNEt)_3$ was vaporized continuously at a rate of 100 μmol/minute at 120° C. with 10 sccm of He carrier gas and directed either to the deposition process or to a process bypass. $NH_3$ was supplied continuously to the process at 10 sccm.

During the periods when precursor was directed to the process, the $NH_3$ was activated only by the temperature of the wafer surface. An increased transmissive optical frequency range was observed, indicating a higher band gap, when the precursor supply time to the wafer was decreased relative to the precursor supply time to the bypass. Alternatively, during the periods where the precursor was directed to the bypass, a hot filament network above the wafer surface was heated to supplement the activation of the $NH_3$. The filament either was made of tungsten and held at 2000K or it was made of Pt and held at 600° C.

The period of time during which the precursor was directed at the process was enough to deposit at least a few monolayers. The period of time during which the precursor was directed to bypass was enough to increase the N:Si ratio to above 1.3. The $NH_3$ supply was constantly directed to the chamber, or diverted to bypass when the precursor was supplied to the wafer surface. Additionally, during the time when the precursor was directed to bypass, the chamber pressure was able to be increased to substantially higher than the deposition pressure (e.g., 100 Torr). The precursor and pulsed nitrogen source were also able to be separated temporally.

EXAMPLE 8

Silicon Nitride Deposition From $(NEt_2)_2ClSi—SiCl(NEt_2)_2$

Figure 11:
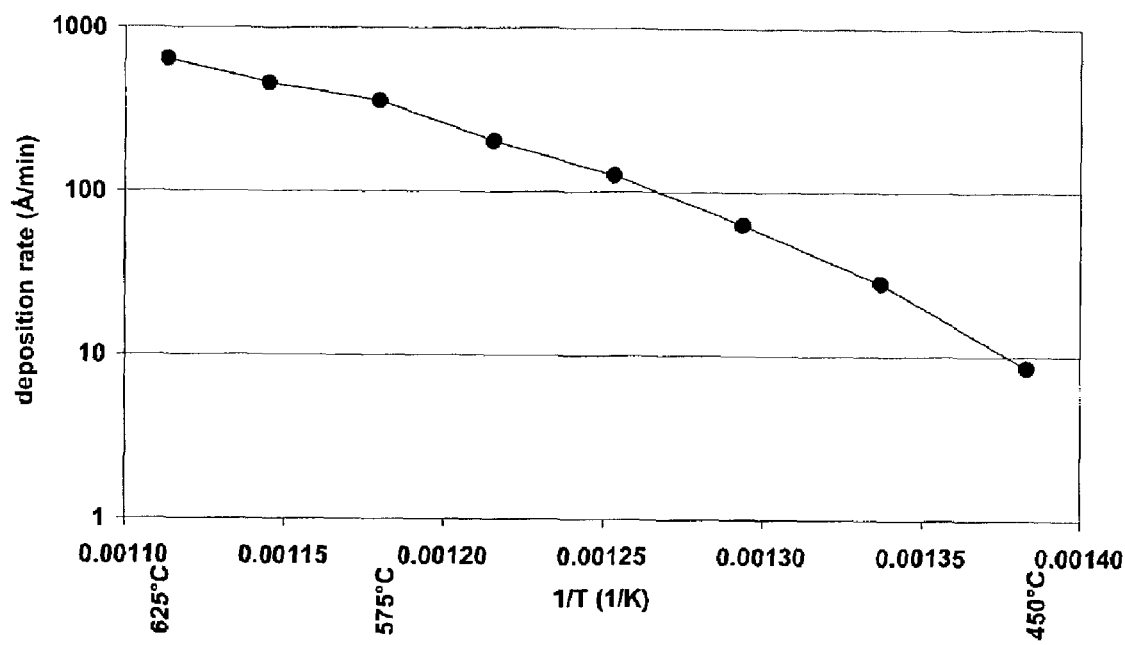
FIG. 11 is a plot of deposition rate as a function of temperature for $(NEt_2)_2ClSi$—$SiCl(NEt_2)_2$ at 10 torr, 10 sccm $NH_3$, 10 sccm He, and 0.2 ml/minute.

A solution of the compound of Example 5, $(NEt_2)_2ClSi—SiCl(NEt_2)_2$, was prepared at a concentration of 0.4M in a hydrocarbon solvent. This solution was metered at 0.2 ml/minute into a vaporizer that was maintained at temperature of 120° C. and had a flow of 10 sccm of He as a carrier gas. The vapor was mixed with 10 sccm of $NH_3$ in a showerhead vapor disperser device that was held at temperature of 120° C., and thereby dispersed over the surface of a heated Si(100) wafer. The chamber pressure was maintained at pressure of 10 torr during deposition. The growth rate of the silicon nitride films decreased from 650 Å/minute at a wafer temperature of 625° C. to 9 Å/minute at 450° C., as shown in FIG. 11. (The index of refraction, n, was >2.2 in all cases, and some films contained Cl.)

EXAMPLE 9

Silicon Nitride Deposition From Cyclotrimethylene-bis(t-butylamino)silane

Figure 12:
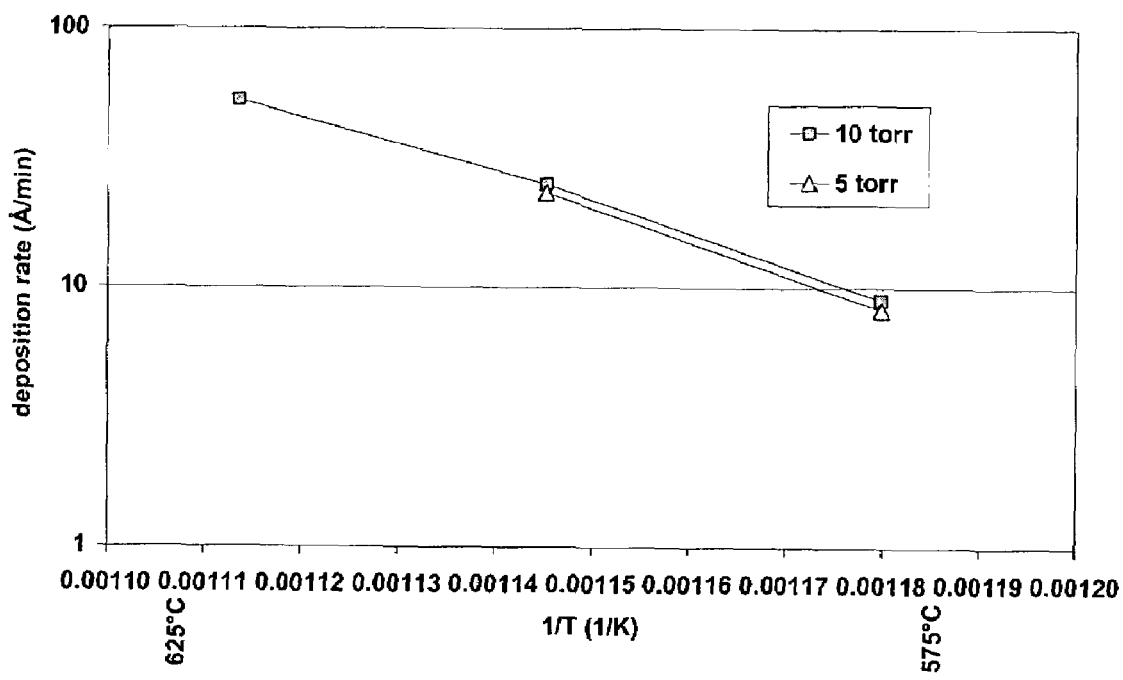
FIG. 12 is a plot of deposition rate as a function of temperature for cyclotrimethylene-bis(t-butylamino)silane at 10 sccm $NH_3$, 10 sccm He, and 0.2 ml/minute.

A solution of the compound cyclotrimethylene-bis(t-butylamino)silane was prepared at a concentration of 0.4M in a hydrocarbon solvent. This solution was metered at 0.2 ml/minute into a vaporizer that was maintained at temperature of 120° C. and had a flow of 10 sccm of He as a carrier gas. The vapor was mixed with 10 sccm of $NH_3$ in a showerhead vapor disperser that was held at temperature of 120° C. and thereby dispersed over the surface of a heated Si(100) wafer. The chamber pressure was maintained at 2, 5, or 10 torr during deposition. The growth rate of the silicon nitride films decreased from 53 Å/minute at a wafer temperature of 625° C. to 9 Å/minute at 575° C. as shown in FIG. 12. There was no measurable effect of pressure on the growth rate, however, which increased from 1.65 to 1.73 as the pressure decreased from 10 torr to 2 torr at 575° C.

EXAMPLE 10

Silicon Nitride Deposition From
η-(N,N-t-butyl)-di(t-butylamino)cyclodisilane

Figure 13:
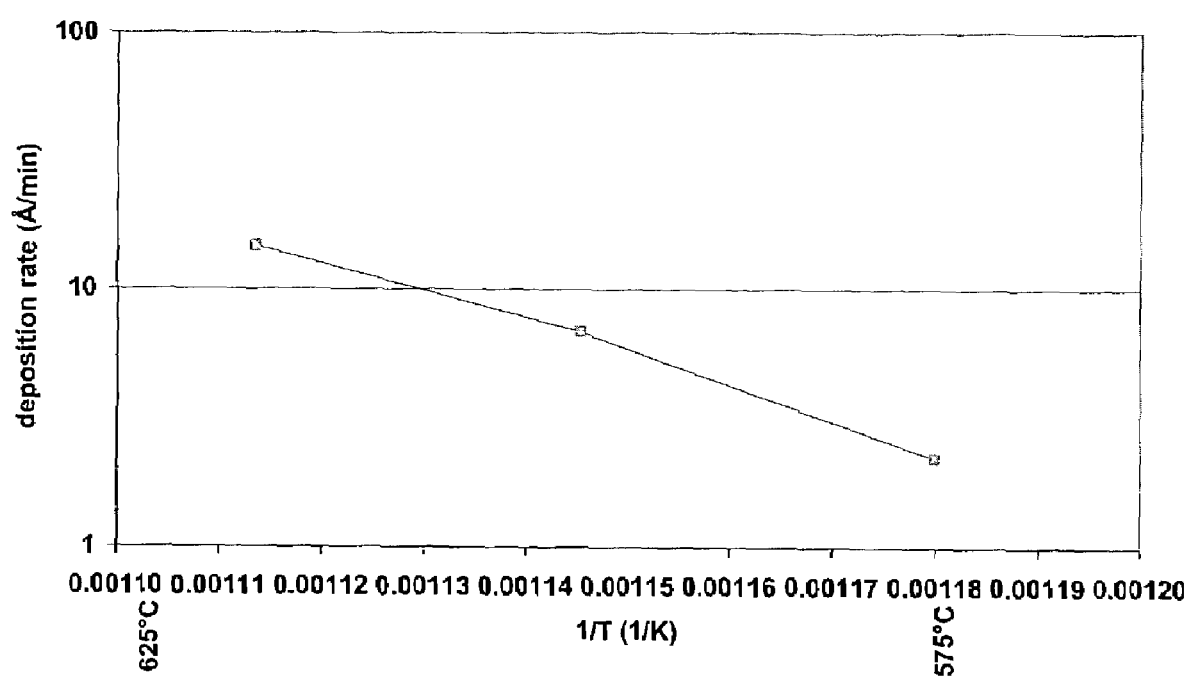
FIG. 13 is a plot of deposition rate as a function of temperature η-(N,N-t-butyl)-di(t-butylamino)cyclodisilane at 10 torr, 10 sccm $NH_3$, 10 sccm He, and 0.2 ml/minute.

A solution of the compound of Example 4, η-(N,N-t-butyl)-di(t-butylamino)cyclodisilane, was prepared at a concentration of 0.4M in a hydrocarbon solvent. This solution was metered at 0.2 ml/minute into a vaporizer that was held at 120° C. and had a flow of 10 sccm of He as a carrier gas. The vapor was mixed with 10 sccm of $NH_3$ in a showerhead vapor disperser that was held at 120° C. and the vapor was thereby dispersed over the surface of a heated Si(100) wafer. The chamber pressure was maintained at 10 torr during deposition. The growth rate of the silicon nitride films decreased from 15 Å/minute at a wafer temperature of 625° C. to 2 Å/minute at 575° C. as shown FIG. 13.

While the invention has been described herein with reference to various specific embodiments, it will be appreciated that the invention is not thus limited, and extends to and encompasses various other modifications and embodiments, as will be appreciated by those ordinarily skilled in the art. Accordingly, the invention is intended to be broadly construed and interpreted, in accordance with the ensuing claims.

What is claimed is:

1. A silicon compound of the formula $$[SiX_n(NR^1R^2)_{3-n}]_2 \qquad (1)$$

wherein:
$R^1$ and $R^2$ may be the same as or different from one another and each is independently selected from the group consisting of H, $C_1$-$C_5$, alkyl, and $C_3$-$C_6$ cycloalkyl;
X is selected from the group consisting of halogen, hydrogen and deuterium; and
$0<n\leq 2$, with the proviso that when $R^1=R^2$=ethyl or methyl, X≠Cl, when $R^1=R^2$=ethyl and n=1 or 2, X≠H, when $R^1=R^2$=isopropyl and n=2, X≠Cl or H, and when $R^1=R^2$=isopropyl and n=1, X≠H.

2. A silicon compound having the formula $(Bu^tNH)_2ClSi$—$SiCl(HNBu^t)_2$.

3. A silicon compound of the formula:

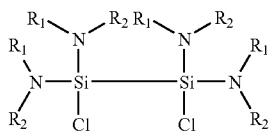

wherein:
$R^1$ and $R^2$ may be the same as or different from one another and each is independently selected from the group consisting of H, $C_1$-$C_5$ alkyl, and $C_3$-$C_6$ cycloalkyl, with the proviso that $R^1$ and $R^2$ cannot simultaneously be ethyl or methyl.

4. A method of forming a silicon-containing film on a substrate, comprising contacting a substrate under chemical vapor deposition conditions including temperature below 600° C. with a vapor of a silicon compound as claimed in claim 1.

5. The method of claim 4, X is chlorine, $R_1$ is H and $R_2$ is tertiary butyl.

6. The method of claim 4, wherein the silicon-containing film comprises a material selected from the group consisting of silicon oxide, silicon oxynitride and silicon and said temperature is <500° C.

7. The method of claim 6, wherein the silicon compound has the formula $(Bu^tNH)_2ClSi$—$SiCl(HNBu^t)_2$.

8. The method of claim 6, wherein the silicon compound comprises a compound of the formula:

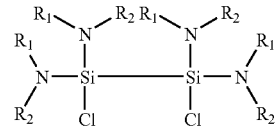

with the proviso that $R^1$ and $R^2$ cannot simultaneously be ethyl or methyl.

9. The method of claim 4, wherein each $R_1$ and $R_2$ are the same as one another.

10. The method of claim 4, wherein each $R_1$ and $R_2$ are different from one another.

11. The method of claim 4, wherein each $R_1$ and $R_2$ is independently selected from $C_1$-$C_5$ alkyl.

12. The method of claim 4, wherein said silicon-containing film comprises a film selected from the group consisting of films, comprising silicon, silicon nitride ($Si_3N_4$), siliconoxynitride ($SiO_xN_y$), silicon dioxide ($SiO_2$), low dielectric constant (k) thin silicon-containing films, high k gate silicate films and low temperature silicon epitaxial films.

13. The method of claim 4, wherein said chemical vapor deposition conditions comprise temperature of from about 400 to about 625° C., pressure of from about 10 to about 100 torr, and the presence of ammonia.

14. The method of claim 4, wherein said chemical vapor deposition conditions comprise temperature of from about 525 to about 625° C., pressure of from about 0.1 to about 10 torr.

15. The method of claim 4, comprising depositing oxynitride deposition of silicon.

16. The method of claim 4, comprising depositing oxynitride deposition of silicate.

17. The method of claim 4, wherein the silicon-containing film comprises silicon nitride.

18. The method of claim 4, wherein said temperature is <500° C.

19. A method of making a compound of the formula:

$$[SiX_n(NR^1R^2)_{3-n}]_2 \qquad (1)$$

wherein:
$R^1$ and $R^2$ may be the same as or different from one another and each is independently selected from the group consisting of H, $C_1$-$C_5$ alkyl, and $C_3$-$C_6$ cycloalkyl;
X is selected from the group consisting of halogen, hydrogen and deuterium; and
$0<n\leq 2$, with the proviso that when $R^1=R^2$=ethyl or methyl, X≠Cl, when $R^1=R^2$=ethyl and n=1 or 2, X≠H, when $R^1=R^2$=isopropyl and n=2, X≠Cl or H, and when $R^1=R^2$=isopropyl and n=1, X≠H,
said method comprising reacting a disilane compound of the formula $X_3Si$—$SiX_3$ with an amine ($R^1R^2NH$) or lithium amide (($R^1R^2N$)Li) compound, wherein X, $R^1$ and $R^2$ are as set out above, according to a reaction selected from the group consisting of the following reactions:

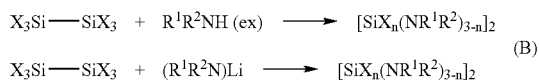

wherein each of the R substituents may be the same as or different from the other and each is independently selected from the group consisting of H, $C_1$-$C_4$ alkyl, and $C_3$-$C_6$ cycloalkyl.

20. The method of claim 4, wherein the silicon compound comprises a precursor that is reacted with a co-reactant in a reaction scheme selected from the group consisting of those of reaction scheme (C) below:

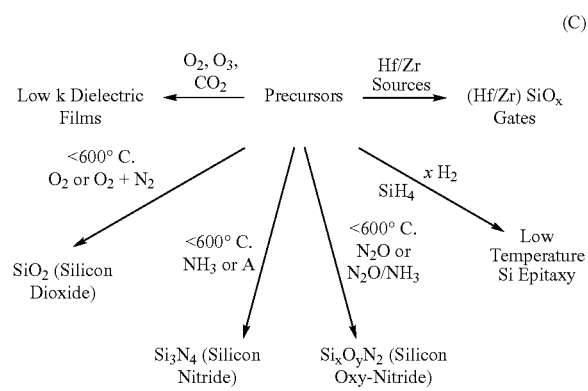

wherein A is selected from the group consisting of $R_3Si-N_3$, $R-N=NR'$ and $R-N=N^+=NR'$, wherein each R is independently selected from the group consisting of $C_1$-$C_3$ alkyl and R' is R or H.

21. A silicon compound of the formula $$[SiX_n(NR^1R^2)_{3-n}]_2 \quad (1)$$

wherein:
$R^1$ and $R^2$ may be the same as or different from one another and each is independently selected from the group consisting of H, $C_3$ alkyl, $C_5$ alkyl, and $C_3$-$C_6$ cycloalkyl;

X is selected from the group consisting of halogen, hydrogen and deuterium; and $0 < n \leq 2$.

22. A composition for delivery of a silicon compound to a substrate, said composition comprising
a) a silicon compound of the formula $$[SiX_n(NR^1R^2)_{3-n}]_2 \quad (1)$$

wherein:
$R^1$ and $R^2$ may be the same as or different from one another and each is independently selected from the group consisting of H, $C_1$-$C_5$ alkyl, and $C_3$-$C_6$ cycloalkyl;

X is selected from the group consisting of halogen, hydrogen and deuterium; and $0 < n \leq 2$, with the proviso that when $R^1=R^2=$ethyl or methyl, $X \neq Cl$, when $R^1=R_2=$ethyl and n=1 or 2, $X \neq H$, when $R^1=R^2=$isopropyl and n=2, $X \neq Cl$ or H, and when $R^1=R^2=$isopropyl and n=1, $X \neq H$; and b) one or more hydrocarbon solvents.

* * * * *